(12) United States Patent
Jago et al.

(10) Patent No.: US 9,734,626 B2
(45) Date of Patent: Aug. 15, 2017

(54) AUTOMATIC POSITIONING OF STANDARD PLANES FOR REAL-TIME FETAL HEART EVALUATION

(71) Applicant: KONINKLIJKE PHILIPS N.V., Eindhoven (NL)

(72) Inventors: James Robertson Jago, Eindhoven (NL); Alasdair Dow, Eindhoven (NL); Antoine Collet Billon, Eindhoven (NL); Lisa Kay Pumphrey, Bainbridge Island, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 139 days.

(21) Appl. No.: 14/646,048

(22) PCT Filed: Nov. 13, 2013

(86) PCT No.: PCT/IB2013/060105
§ 371 (c)(1),
(2) Date: May 20, 2015

(87) PCT Pub. No.: WO2014/080319
PCT Pub. Date: May 30, 2014

(65) Prior Publication Data
US 2015/0302638 A1  Oct. 22, 2015

Related U.S. Application Data

(60) Provisional application No. 61/728,566, filed on Nov. 20, 2012.

(51) Int. Cl.
*G06T 17/00* (2006.01)
*A61B 8/08* (2006.01)
(Continued)

(52) U.S. Cl.
CPC ............ *G06T 17/00* (2013.01); *A61B 8/0866* (2013.01); *A61B 8/145* (2013.01); *A61B 8/483* (2013.01);
(Continued)

(58) Field of Classification Search
None
See application file for complete search history.

(56) References Cited

U.S. PATENT DOCUMENTS

| | | | |
|---|---|---|---|
| 5,207,225 A | * | 5/1993 | Oaks .................. A61B 8/12 600/443 |
| 5,997,479 A | | 12/1999 | Savord et al. |

(Continued)

FOREIGN PATENT DOCUMENTS

| WO | 2007034425 A2 | 3/2007 |
|---|---|---|
| WO | 2011001309 A1 | 1/2011 |

OTHER PUBLICATIONS

"Automatic Alignment of Standard Views in 3D Echocardiograms Using Real-Time Tracking" Orderud et al, Proceedings of SPIE, vol. 7265, Feb. 26, 2009.

(Continued)

*Primary Examiner* — Anh-Tuan V Nguyen

(57) ABSTRACT

An ultrasound system and method are described for acquiring standard views of the fetal heart simultaneously with real-time imaging. A matrix array probe is manipulated until a first standard view such as a 4-chamber view is acquired. The first standard view image is matched to its corresponding plane in a fetal heart model. From the matched plane of the heart model, the orientations of the other standard views are known from the geometrical relationships of structures within the heart model. This orientation information is used (Continued)

to control the matrix array probe to automatically scan the planes of all of the standard views simultaneously in real-time.

15 Claims, 6 Drawing Sheets

(51) Int. Cl.
  *A61B 8/14*  (2006.01)
  *A61B 8/00*  (2006.01)
  *G06T 19/00*  (2011.01)
  *G06T 15/08*  (2011.01)
  *G06T 7/30*  (2017.01)

(52) U.S. Cl.
  CPC .................. *A61B 8/54* (2013.01); *G06T 7/30* (2017.01); *G06T 15/08* (2013.01); *G06T 19/00* (2013.01); *F04C 2270/0421* (2013.01); *G06T 2207/10132* (2013.01); *G06T 2207/30048* (2013.01); *G06T 2210/41* (2013.01); *G06T 2219/028* (2013.01)

(56) References Cited

U.S. PATENT DOCUMENTS

| | | |
|---|---|---|
| 6,436,048 B1 | 8/2002 | Pesque |
| 6,669,641 B2 | 12/2003 | Poland et al. |
| 6,709,394 B2 | 3/2004 | Frisa et al. |
| 6,755,786 B2 | 6/2004 | Frisa et al. |
| 2004/0254439 A1 | 12/2004 | Fowkes |
| 2005/0004446 A1* | 1/2005 | Cowan ................. G06F 19/321 600/407 |
| 2005/0004465 A1 | 1/2005 | Abuhamad |
| 2005/0251036 A1* | 11/2005 | Abuhamad ............. A61B 8/08 600/437 |
| 2005/0283079 A1* | 12/2005 | Steen ....................... A61B 8/14 600/447 |
| 2007/0249935 A1* | 10/2007 | Deschinger .......... A61B 8/0866 600/437 |
| 2008/0009722 A1* | 1/2008 | Simopoulos ............. A61B 8/08 600/437 |
| 2008/0304744 A1 | 12/2008 | Peters et al. |
| 2010/0172559 A1* | 7/2010 | Kumar ................ A61B 10/0241 382/131 |
| 2011/0021903 A1* | 1/2011 | Strommer ............... A61B 5/042 600/410 |
| 2011/0118595 A1* | 5/2011 | Aulbach ................ A61B 6/032 600/425 |
| 2011/0201935 A1 | 8/2011 | Collet-Billon et al. |
| 2011/0206255 A1* | 8/2011 | Buelow .................. G06T 7/0012 382/128 |
| 2011/0317897 A1* | 12/2011 | Narasimhamurthy G06T 7/2006 382/131 |
| 2012/0078097 A1* | 3/2012 | Wang ..................... G06T 7/2046 600/437 |
| 2012/0089027 A1* | 4/2012 | Andreuccetti ........... A61B 8/06 600/443 |
| 2012/0123267 A1* | 5/2012 | Dow ......................... A61B 8/02 600/443 |
| 2012/0157845 A1* | 6/2012 | Rabben .................... A61B 8/08 600/443 |
| 2013/0094749 A1* | 4/2013 | Oh .......................... A61B 6/503 382/133 |
| 2014/0050381 A1* | 2/2014 | Lee ....................... A61B 8/5223 382/131 |
| 2015/0016704 A1* | 1/2015 | Weese ................... G06T 7/0028 382/131 |

OTHER PUBLICATIONS

"Operator Gudance in 2D Echocardiography Via 3D Model." Bergmeir et al , Proceedings of SPIE, vol. 7265, Feb. 26, 2009.
"Automatic MPR Automatic Detection of Standard Planes in 3D Echocardiography" Lu et al, From Nano to Macro 2008, IEEE International Symposium on Biomedical Imaging, May 14, 2008., p. 1279-1282.
"Automated Selection of Standardized Planes From Ultrasound Volume" Rahmatullah et al, Sep. 18, 2011 Machine Learning in Medical Imaging p. 35-42.
"Supporting Ultrasound Diagnosis Using an Animated 3D Model of the Heart" Berlage et al, Proceedings of the ThirdIEEE InternationalConference on Multimedia Computing and Systems, Jan. 1, 1996, p. 34-39.

* cited by examiner

AUTOMATIC POSITIONING OF STANDARD PLANES FOR REAL-TIME FETAL HEART EVALUATION

This application is the U.S. National Phase application under 35 U.S.C. §371 of International Application No. PCT/IB2013/060105, filed on Nov. 13, 2013, which claims the benefit of U.S. Provisional Application No. 61/728,566 filed on Nov. 20, 2012. These applications are hereby incorporated by reference herein.

This invention relates to medical diagnostic ultrasound systems and, in particular, to ultrasound systems which can perform diagnosis of the fetal heart by real-time imaging of diagnostically useful image planes.

Ultrasonic imaging is routinely used during pregnancy to assess the development of the fetus in the mother's womb. Fetal cardiac ultrasound screening is intended for the detection of structural anomalies (generally congenital heart defects, or CHD) and includes the analysis of standard two dimensional (2D) image views of the fetal heart. Typical standard views include the 4-chamber view and views which enable the assessment of the left ventricle (LV) and right ventricle (RV) outflow tracts. Other views which may be required include a 5-chamber view, a 3-vessel view, and a tracheal view. In practice, these views usually reveal most CHDs. The traditional way for the clinician to an acquire an image of each required view is to manipulate the ultrasound probe while in acoustic contact with the abdomen until a desired anatomical orientation is in the plane of the 2D imaging probe. For instance, the clinician first manipulates the probe until the fetal heart is seen in a 4-chamber view. The clinician then stores an image of that view or a sequence of images over one or more heartbeats. Image storage is ended and the clinician manipulates the probe again, this time trying to align the image plane with a view of the LV outflow tract. When the clinician has successfully aligned the image plane with this view, another image or sequence of images are stored. The process of probe manipulation and storage is repeated for a third and other views as required. With this procedure, there can be a substantial number of cases of missed abnormalities because obtaining and analyzing these views require high skill: fetal echocardiography is very operator-dependent. In addition, the fetus may be moving during the procedure, requiring the clinician to reorient herself with the fetal heart each time the fetus moves.

With the advent of three dimensional (3D) ultrasound image acquisition (notably the Spatial Temporal Image Correlation, or STIC, protocol) it is now possible to capture the entire volume of the fetal heart and adjacent vessels and to perform computed reconstruction of 2D views at any orientation in the heart, including the standard ones, even after the patient is released. The STIC procedure is conducted by making a slow sweep of the 2D image plane over the fetal heart, which may take 10 seconds or more. The objective is to acquire an image of each adjacent anatomical plane of the fetal heart at each phase of the fetal heart cycle. This is done by acquiring a large number of images over many heart cycles as the image plane is swept over the heart. User-directed image processing is then used to extract the predominant temporal cycle of the entire fetal heart from the acquired 2D frames. This information is then used to re-assemble the frames into a series a volume images, each at a different phase of the heart cycle. The standard 2D views are then extracted from the volumes by the user by a process known as multiplanar reconstruction (MPR). The clinician must search through the volumes at different plane orientations, searching for each standard view. Some views may be distorted or anatomically incorrect, depending on the speed and uniformity of the sweep of the image plane. The quality and consistency of the STIC volumes can vary greatly from one exam to the next. Furthermore, the STIC images are not in real time, but are synthesized retrospective reconstructions of the anatomical views constructed from multiple, different heart cycles. Despite the difficulties and limitations of the STIC procedure, it is now accepted practice that 3D fetal heart exams can potentially reduce misdiagnosis rate and improve workflow and operator dependency (less skills), provided that the 3D workflow is intuitive and adequate tools (e.g., MPR) are provided to explore the volumetric image data.

One might think that real-time 3D ultrasonic imaging could be used to acquire live volume images of the fetal heart. Unfortunately, current volume frame rates are not high enough, in most cases, to provide both sufficient spatial resolution and temporal resolution (volume rate) to make live 3D imaging practical for fetal heart imaging. Furthermore, since only certain 2D image planes are required to diagnose the fetal heart, much of the 3D information is not utilized. If one could acquire just the planes needed, in principle these could be acquired at much higher frame rates and with much better resolution. Hence there is a need to be able to acquire, with good spatial and temporal resolution, ultrasound data that provides the required 2D standard views simultaneously in real-time.

In accordance with the principles of the present invention, a diagnostic ultrasound system and method are described which enables acquisition of multiple standard views of target anatomy such as the fetal heart in real-time. A matrix array probe is placed in contact with a suitable acoustic window on the mother's body to view the fetal heart. A matrix array probe is capable of scanning selectable, differently oriented image planes in rapid succession, enabling real-time imaging of the selected image planes. The probe is first manipulated while imaging one plane in real-time until a first reference plane such as a 4-chamber view is acquired. A model of the target anatomy such as a heart model is then used to match the ultrasound image of the 4-chamber view with a corresponding 4-chamber view in the heart model. From the relative orientation of desired planes in the model, the heart model provides information as to the relative orientations of other standard views in relation to the acquired reference plane. This information is used to control the matrix array probe to additionally scan the image planes of one or more other views in real-time. The user can then display the reference standard view and one or more other desired views simultaneously in real-time.

Figure 1:
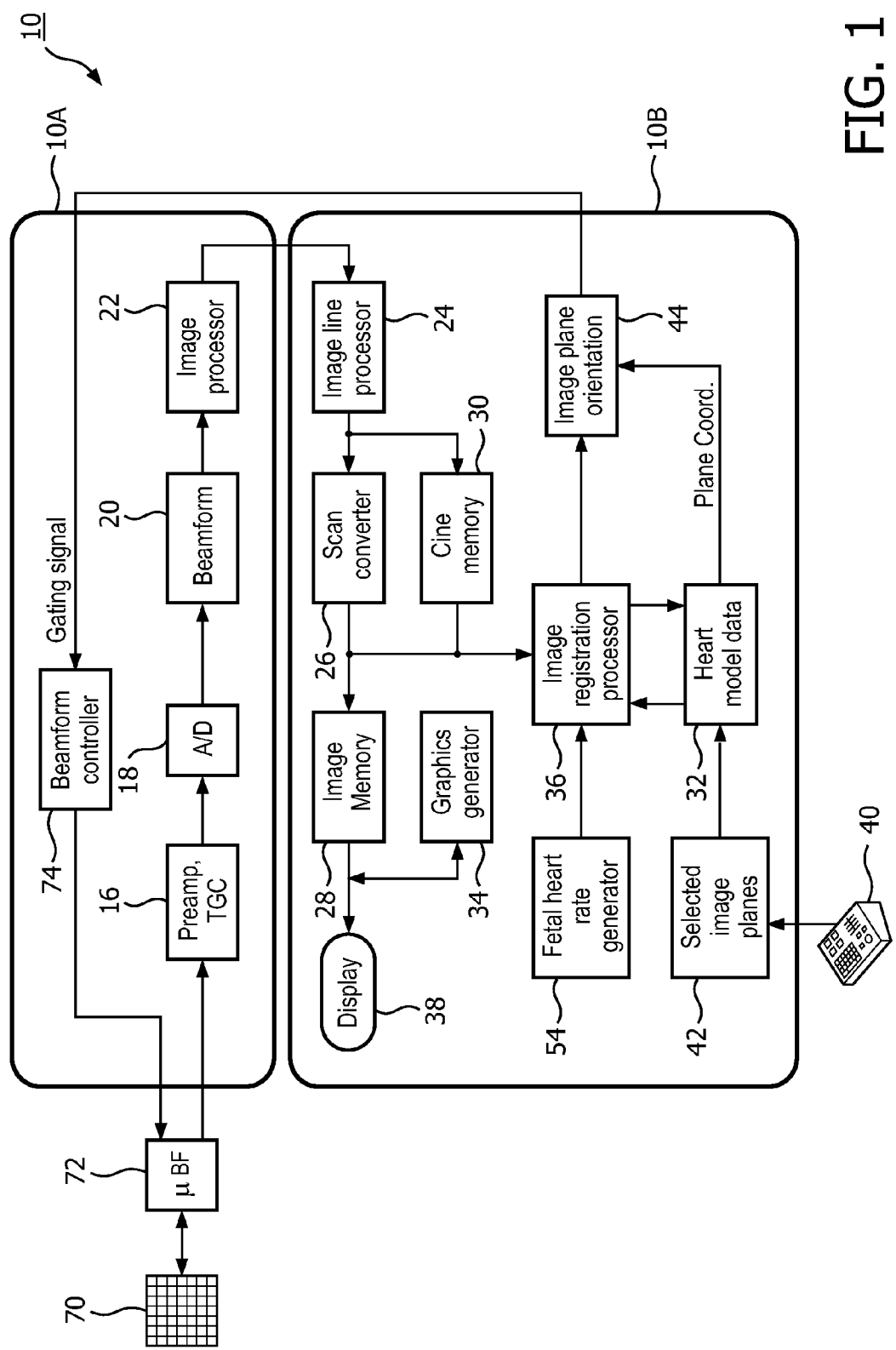
FIG. 1 illustrates in block diagram form an ultrasound system constructed in accordance with the principles of the present invention.

Referring first to FIG. 1, an ultrasound system 10 constructed in accordance with the principles of the present invention is shown in block diagram form. The ultrasound system is configured by two subsystems, a front end acquisition subsystem 10A and a display subsystem 10B. An ultrasound probe is coupled to the acquisition subsystem which includes a two-dimensional matrix array transducer 70 and a micro-beamformer 72. The micro-beamformer contains circuitry which control the signals applied to groups of elements ("patches") of the array transducer 70 and does initial processing of the echo signals received by elements of each group. Micro-beamforming in the probe advantageously reduces the number of conductors in the cable between the probe and the ultrasound system and is described in U.S. Pat. No. 5,997,479 (Savord et al.) and in U.S. Pat. No. 6,436,048 (Pesque).

The probe is coupled to the acquisition subsystem 10A of the ultrasound system. The acquisition subsystem includes a beamform controller 74 which is responsive to a gating signal produced as described below and provides control signals to the microbeamformer 72, instructing the probe as to the timing, frequency, direction and focusing of transmit beams in 2D image planes or 3D volumes. The beamform controller also controls the beamforming of echo signals received by the acquisition subsystem by its control of analog-to-digital (A/D) converters 18 and a beamformer 20. Echo signals received by the probe are amplified by preamplifier and TGC (time gain control) circuitry 16 in the acquisition subsystem, then digitized by the A/D converters 18. The digitized echo signals are then formed into fully steered and focused beams by a beamformer 20. The echo signals are then processed by an image processor 22 which performs digital filtering, B mode detection, and Doppler processing, and can also perform other signal processing such as harmonic separation, speckle reduction, and other desired image signal processing.

The echo signals produced by the acquisition subsystem 10A are coupled to the display subsystem 10B, which processes the echo signals for display in the desired image format. The echo signals are processed by an image line processor 24, which is capable of sampling the echo signals, splicing segments of beams into complete line signals, and averaging line signals for signal-to-noise improvement or flow persistence. The image lines for a 2D image are scan converted into the desired image format by a scan converter 26 which performs R-theta conversion as is known in the art. The image is then stored in an image memory 28 from which it can be displayed on a display 38. The image in memory is also overlaid with graphics to be displayed with the image, which are generated by a graphics generator 34. Individual images or image sequences can be stored in a cine memory 30 during capture of image loops or sequences.

In some implementations it may be desirable to acquire images at particular phases of the fetal heart cycle. A fetal heart rate generator 54 provides this capability. The fetal heart rate generator synthesizes the periodicity of the fetal heart cycle as described in international patent publications WO 2011/001309 (Jago et al.) and WO 2011/158136 (Schauf). The fetal heart rate generator produces a gating signal at a selected phase of the fetal heart which can be used to gate image acquisition or processing as described below.

In accordance with the principles of the present invention, the display subsystem includes heart model data 32 of the fetal heart. The heart model data is that of a 3D anatomical mesh model of the fetal heart as described in US patent pub. no. 2008/0304744 (Peters et al.) and in U.S. provisional application No. 61/569,450, filed Dec. 12, 2011 (Radulescu et al.) Such a model represents the structure of the heart including its interior and exterior structure such as blood vessels and valves. The heart model may be of a single phase of the heart such as end diastole, or it may comprises multiple models of the heart at different phases of the heart cycle. Importantly for the present invention, individual planes can be extracted from the heart model data and matched or registered to actual fetal ultrasound 2D images. This registration is performed by an image registration processor 36, which receives ultrasound images of a fetal heart produced by the scan converter 26 and registers them with a corresponding plane of the heart model data. A match with a plane of the heart model triggers the production of image plane orientation data 44, which in turn couples image plane coordinates or orientation data in a gating signal to the beamform controller 74 which in response directs the matrix array probe to scan an identified image plane. Plane coordinate information for the image plane orientation is provided from the heart model data. The heart model data 32 is accessed for selected image planes 42 which are selected from the user control panel 40. The ECG trigger signal generator 54 is coupled to the image registration processor 36.

Figure 2:
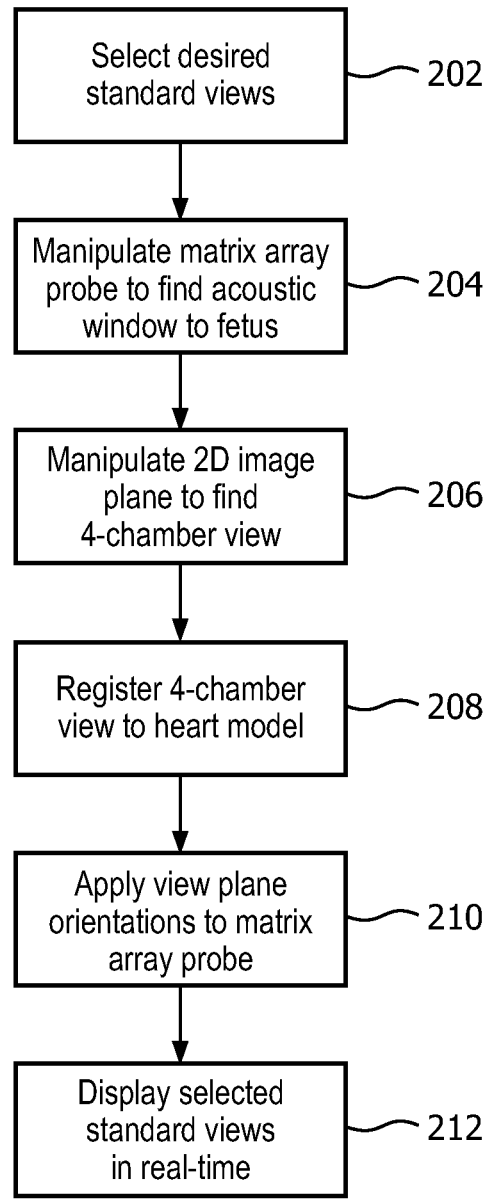
FIG. 2 illustrates one method for fetal image acquisition and display in accordance with the present invention.
Figure 5A:
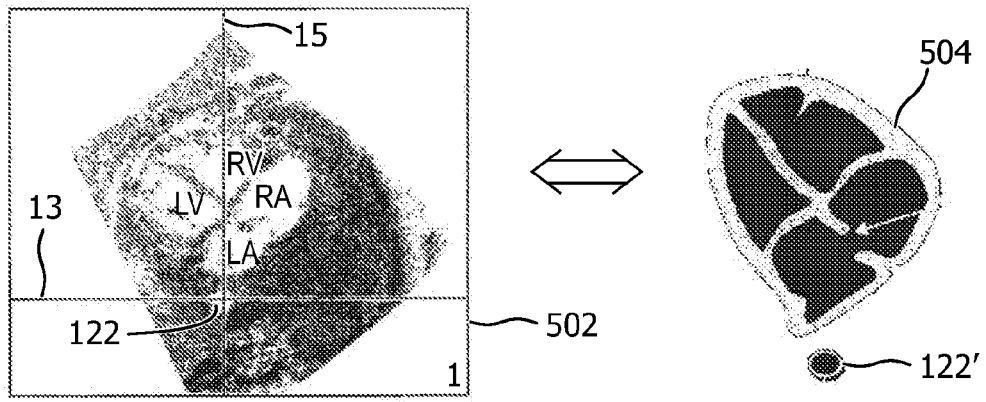
FIG. 5 illustrates three standard views of a fetal heart in association with their corresponding planes of a fetal heart model.
Figure 5B:
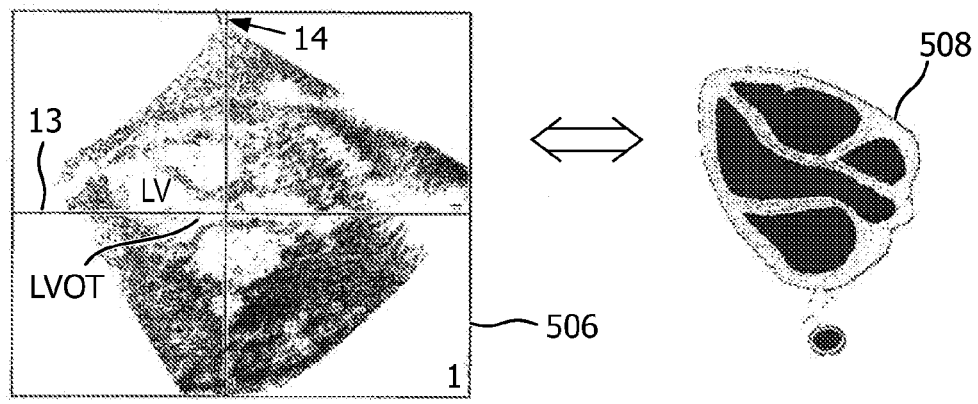
Figure 5C:
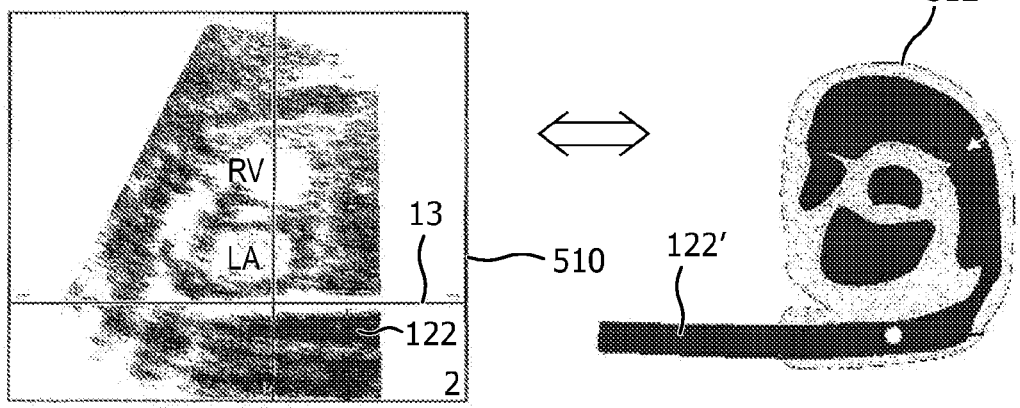

One method for using the ultrasound system of FIG. 1 to acquire standard images for a fetal heart exam is illustrated in FIG. 2. In step 202 the user selects the standard views that are desired for this particular fetal heart exam. As mentioned above, typical standard views include a 4-chamber view, LV outflow tracts, RV outflow tracts, 5-chamber view, 3-vessel view, and the tracheal view. The user may select these standard views from a list of standard views accessed as a pull-down list on the system display. The user selects the desired views with a control of control panel 40, and the image planes of the selected views are stored at 42 where they are used to select the views from the planes of the heart model data 32. In step 204 the user presses the matrix array probe aperture against the abdomen of the patient and manipulates the probe until a suitable acoustic window is found, one from which the user can image the fetal heart. In step 206 the user manipulates the matrix array probe, which at this time is only scanning a single 2D image plane, until the image plane is intersecting the fetal heart and an image of the first selected view of the heart is obtained. Typically this first standard view will be a 4-chamber view of the fetal heart. This first standard view is coupled to the image registration processor 36 which, in step 208, registers the ultrasound image with a plane of the heart model. Registration of an ultrasound image with a heart model is described in the above Peters et al. publication and Radulescu et al. application and is visually illustrated in position a) of FIG. 5. On the left side of position a) is a 4-chamber ultrasound image 502 of the fetal heart, and on the right side of position a) is a 4-chamber plane 504 of a 3D fetal heart model. The heart model plane 504 is oriented with the cross-section of the descending aorta 122' at the bottom, in correspondence with its location at 122 in the ultrasound image 502. The heart chambers in the ultrasound image have been labeled (RA, LA, RV, LV), and their correspondence with those of the heart model plane 504 is readily apparent. Thus the image registration processor identifies a plane of the heart model which most closely matches the anatomy of the 4-chamber view 502, using tools such as block matching of the pixels of the ultrasound image to different planes through the heart model data. The arrow in the heart model plane 504 and in other illustrated heart model planes indicate anatomical landmarks in the heart model planes which can be most readily found and matched in ultrasound images, speeding the registration process. FIG. 5 also illustrates the matching of other standard views to a heart model. Position b) illustrates an image 506 of the LV outflow tract in correspondence with an LV outflow tract plane 508 of a fetal heart model, and position c) illustrates an image 510 of a ductal arch view in correspondence with a ductal arch plane 512 of the heart model. The ductal arch image 510 is seen to be reversed in relation to the plane 512 of the heart model. This can be resolved by reversing the ultrasound image as described in U.S. Pat. No. 6,669,641 (Poland et al.), or by reversing the heart model data during the registration process as described in the above-referenced Peters et al. publication and Radulescu et al. application.

Once a heart model plane had been found which best matches the anatomy of the first standard view ultrasound image, the orientations of the other selected standard views can be readily identified using the heart model. When the first standard view plane has been identified in the heart model, the relative orientations of other standard view planes are known from the heart model, based on a priori statistical knowledge about the normal geometrical relationships of structures within the fetal heart. For example, when a particular plane of the heart model is identified as the 4-chamber view, the next standard view may be in a plane that is rotated 35° and tilted 15° with respect to the 4-chamber view plane in the model, for instance. The coordinates of this rotated and tilted plane are coupled to the image plane orientation data 44 and used to control the matrix array probe to scan a second image plane in this particular orientation relative to the first standard view plane. Similarly, the plane coordinates of other selected standard planes are found in the heart model data, coupled to the image plane orientation data, and used to gate the scanning of additional image planes in all selected standard view planes, as indicated in step 210.

Figure 6:
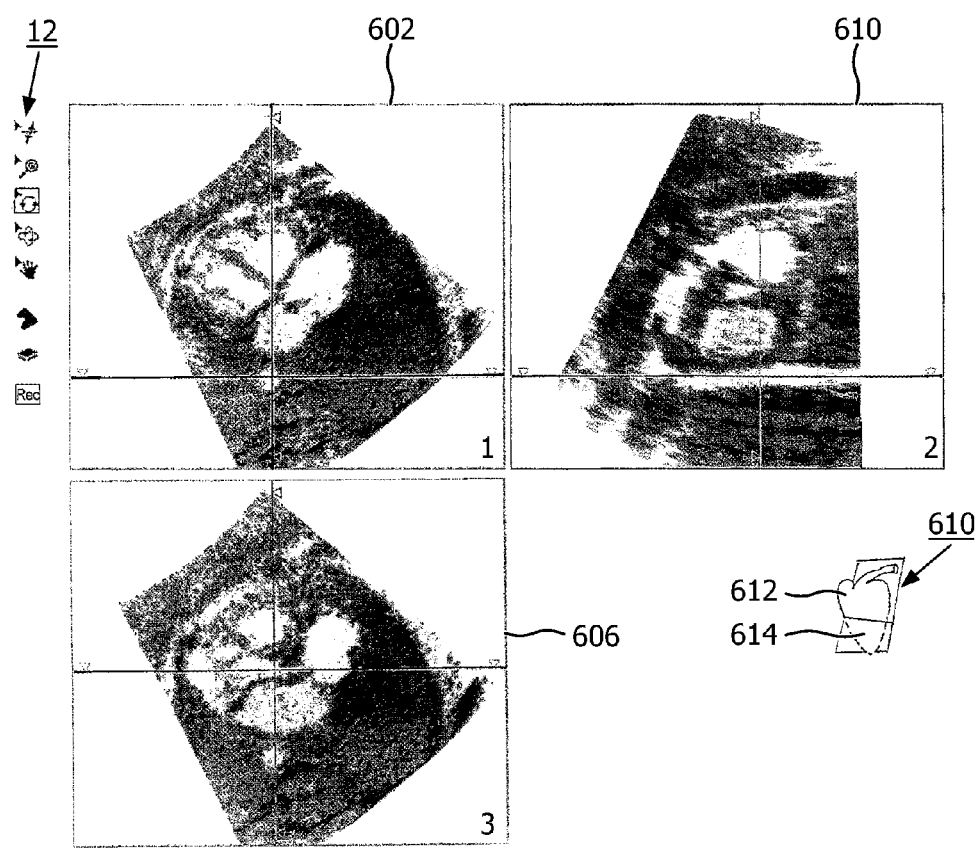
FIG. 6 illustrates an ultrasound system display with three real-time views of standard image planes of a fetal heart produced in accordance with the principles of the present invention.

In step 212 the selected standard views are displayed in real-time on the ultrasound display 38. FIG. 6 illustrates the display screen of an ultrasound system which is displaying three such standard views in real-time. In the upper left quadrant of the screen a live 4-chamber view 602 is shown, in the upper right quadrant a live ductal arch view 610 is shown, and in the lower left quadrant a LV outflow view 606 is shown. The three views can be simultaneously displayed in real-time because only three image planes need to be scanned in alternating succession, rather than an entire 3D volume from which MPR frames must be identified and extracted. When the 4-chamber view 602 is used as the starting standard view, the other standard views will generally be in planes which also intersect the transducer aperture, enabling all of the standard views to be imaged as B mode images. This is most desirable, as a C mode image would require virtually the same scanning time as a full volume and the high frame rate advantage of only scanning a few planes would be lost. The implementation of FIG. 6 contains an icon graphic 610 of a generic fetal heart 612 which shows the user how the planes 614 of the images intersect the heart. The outline of the fetal heart graphic 612 can be provided by the fetal heart model 32. Each image in FIG. 6 is outlined by a box. When the user clicks on an image, its box is highlighted, indicating that the plane graphic 614 is showing the orientation of that image in relation to the heart. Alternatively, each box can be outlined by a different color, and multiple like-colored plane graphics 614 can be displayed in the graphic simultaneously. Another display option is to render the three planes in three dimensions, depicting the relative orientation of all three real-time images to the user. The real-time images can also be overlaid with adjustable cursors 13, 14, and 15 (see FIG. 5) which can be repositioned by the user and clicked on using image adjustment controls 12 to view image planes orthogonal to the standard view planes. Another graphic which is commonly displayed with the images is the fetal heart rate, produced by the fetal heart rate generator 54, which is an important factor in many diagnoses.

In principle, the operation and control of the matrix array probe in an implementation of the present invention can use elements of the functionality of a matrix array probe when operated in the biplane mode. U.S. Pat. No. 6,669,641 (Poland et al.), U.S. Pat. No. 6,709,394 (Frisa et al.) and U.S. Pat. No. 6,755,786 (Frisa et al.) describe ultrasonic biplane imaging. In biplane imaging a two-dimensional matrix array transducer probe scans two different 2D image planes in rapid alternating succession, thereby producing live real-time images of both planes. One of the image planes is denominated as the reference image plane. This image plane is generally oriented perpendicular to the plane of the matrix array transducer, extending straight out from the probe around a center orthogonal axis to the array. The reference image orientation is usually maintained stationary and the second image plane is movable by the user in relation to this reference plane. The '394 patent describes biplane imaging in which the second image plane can be tilted or rotated with respect to the reference plane. In a commercial embodiment available from Philips Healthcare of Andover, Mass., the tilted image plane has a nominal orientation with its center axis in alignment with the center axis of the reference plane. The tilt plane can be moved (tilted) so that it is oriented at different angles in relation to the center axis of the reference plane but with its center axis always located in the reference plane. The rotational biplane implementation again has the center axis of the second (rotating) image plane aligned at the start with the center axis of the reference image and the second image orientation is orthogonal to the plane of the reference image. From this starting position the rotating plane can be rotated about its center axis at angles with respect to the reference image which vary from orthogonal. The '786 patent describes what is known as elevation tilt biplane imaging. In elevation tilt imaging the second image has a starting position in alignment with the reference image. The second image is then moved away from the reference image plane in the elevation dimension, and can be moved to different planes which do not intersect the reference image plane in the region of interest. The two planes can thus be perfectly parallel or angularly parallel, the latter being a condition where the second plane has a common apex location with the reference plane or intersects the reference plane above the top (shallowest depth) of the images. Biplane images allow a clinician to position the reference plane to view a target anatomy or region of interest, then move the second plane to observe other planar images of the target anatomy. As shown in the foregoing patents, the two biplane images are displayed side-by-side at the same time, so that the clinician can constantly view the reference image while moving the second plane. Biplane imaging allows the clinician to scan and observe two image planes at the same time, while constantly maintaining his or her navigational bearings of the image locations within the three dimensional volume being scanned. When the clinician locates anatomy of interest in both image planes, a single image or a loop (sequence of live images) can be captured or save and displayed or replayed later when making a definitive diagnosis. An implementation of the present invention can use two (biplane) images when only two standard views are required, and is extended to image further planes when three or more standard views are needed. The central reference image plane of biplane imaging can be used to acquire the starting standard view such as the 4-chamber view. When the 4-chamber view is seen in the reference image, the image registration processor 36 matches the image to the closest 4-chamber plane of the heart model and the heart model provides the relative orientations of the other desired standard views from their positions in the heart model. These plane orientations are coupled to the beamform controller 74, which then automatically begins scanning and displaying images of these other views in real-time. If the fetus moves during the exam, the user only has to reposition the probe to reacquire the 4-chamber view in the reference image plane, the image registration processor again matches the image to a 4-chamber plane of the heart model, the orientations of the other standard views are identified in the heart model, coupled to the beamform controller, and live imaging of all of the standard views resumes.

An implementation of the present invention can operate with a fixed heart model or one that is adaptable. For example, the heart model may be one which represents the heart at the end diastole phase of the heart cycle. The image registration process is then done with an image captured at that phase of the fetal heartbeat. This can be done by use of the fetal heart rate generator 54, which can gate images at selected phases of the fetal heart cycle, which enables the registration processor to perform a match at the moment when an end diastole image has been acquired.

Figure 3:
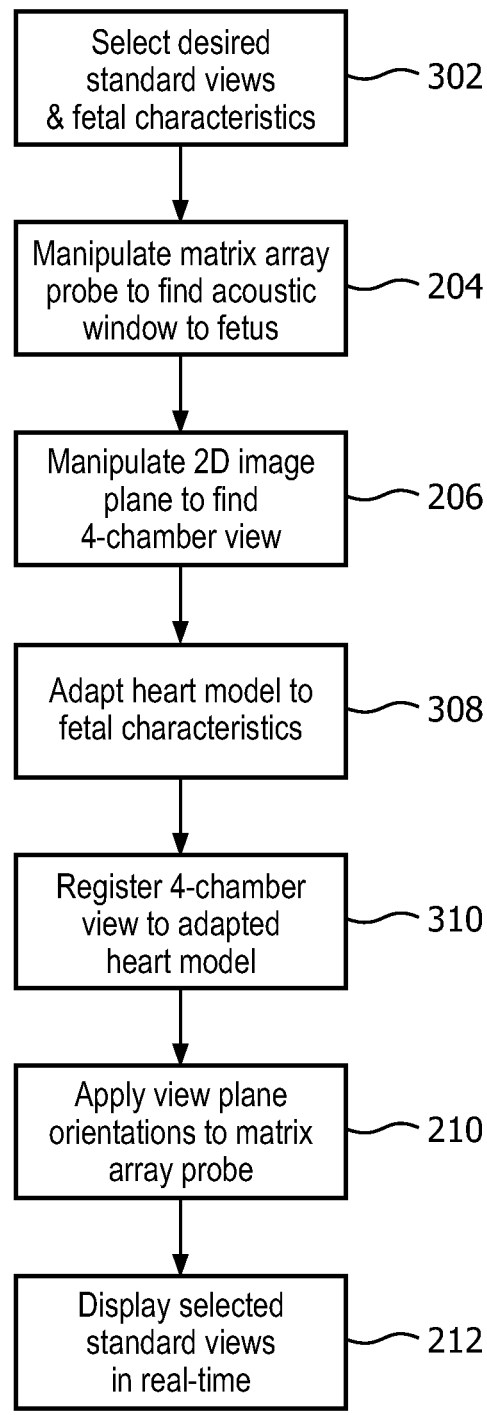
FIG. 3 illustrates a second method for fetal image acquisition and display in accordance with the present invention.

FIG. 3 illustrates a method of the present invention where the heart model is adapted to the particular fetus. In the setup step 302 the user not only selects the standard views that are desired, but also enters fetal characteristics such as fetal age, shape and development of the fetal heart, known or suspected heart abnormalities or defects, or other information which more particularly describes the heart of the fetus to be examined. This information is then used in step 308 to adapt the heart model to the particular fetus. One adaptation technique is to have a library of different fetal heart models for different fetal ages. Entry of fetal age data enables the selection of the heart model which most closely matches the age of the fetus being examined, making image registration easier and more reliable. Another adaptation technique is to morph or warp the heart model to the size and shape of the features in an acquired fetal heart image, as described in the above-referenced Peters et al. publication and Radulescu et al. application. See also international patent publication WO 2007/034425 (Ecabert et al.) A given heart model can be adapted to virtually any fetal heart images and to different phases of the heart cycle. A starting standard view image is registered to the adapted heart model data in step 310 and identification, scanning and display of the other standard view images proceeds in steps 210 and 212 as before.

Figure 4:
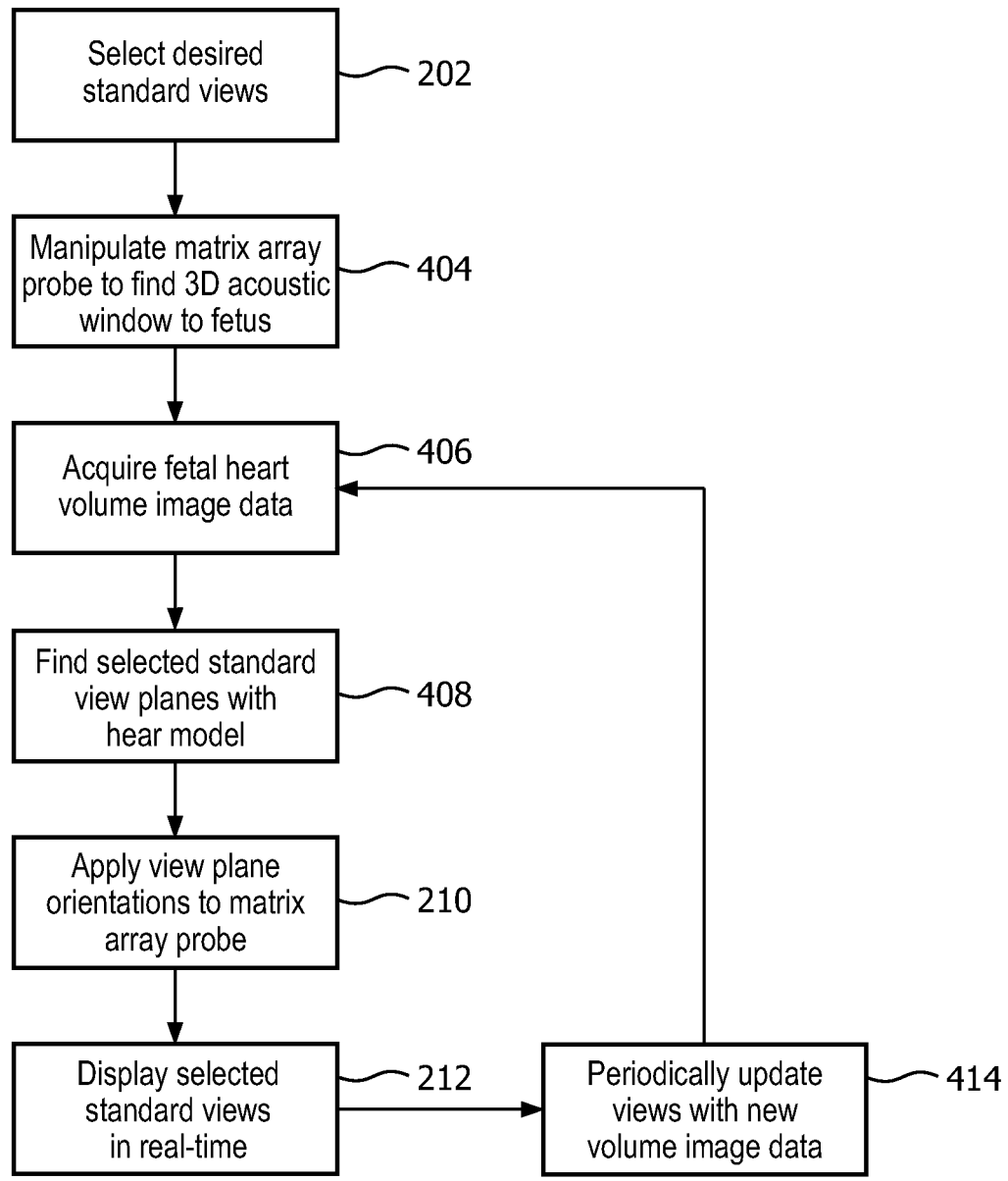
FIG. 4 illustrates a third method for fetal image acquisition and display in accordance with the present invention.

FIG. 4 illustrates an even more highly automated implementation of the present invention. In this method the user begins imaging, not in 2D, but in 3D acquisition mode. In step 404 the user finds an appropriate 3D acoustic window from which to image the entire fetal heart in 3D, and in step 406 a volume image of the fetal heart is acquired. The registration processor then matches at least one plane of the volume image, as by MPR reconstruction, for instance, with a corresponding plane of the heart model 32. The standard view planes are then identified in the heart model, either by matching all of the standard view planes of the volume ultrasound image to corresponding planes of the heart model, or by the relative orientations of standard view planes of the heart model to one ultrasound image-heart model plane match. The orientations of the standard view planes are supplied to the matrix array probe (step 210), which begins scanning and displaying the selected standard view 2D planes (step 212). With this implementation the user does not have to find even an initial standard view. It is only necessary to capture volume image data of the fetal heart, and the ultrasound system identifies and extracts the desired standard view planes and begins imaging them without further user input. The method of FIG. 4 can also incorporate adaptation of the heart model as discussed in the description of FIG. 3.

To account for movement of the probe or fetus in the method of FIG. 4, the matrix array probe periodically acquires another volume image dataset in step 414. The new volume image data is used again starting with step 406 to re-identify the orientations of the standard view planes and updates the control of the matrix array probe to image the desired standard view planes. It is only necessary for the user to position the probe so that a full volume image dataset can be continually acquired as needed. Thus, the system can continue to track and display the desired standard views in real-time without any user interaction, simplifying and accelerating the ability to make a diagnosis of the fetus.

What is claimed is:

1. A diagnostic ultrasound system for imaging multiple planes of a target anatomy comprising:
a matrix array probe configured to scan a plurality of image planes in real-time in a region of a body;
a beamform controller configured to control scanning by the matrix array probe;
an image processor, coupled to the matrix array probe, configured to produce real-time ultrasound images of the plurality of image planes scanned by the matrix array probe;
a display, coupled to the image processor, for simultaneously displaying the ultrasound images in real-time;
data representing an anatomical model of the target anatomy;
an image registration processor configured to register an ultrasound image with the data representing the anatomical model, generate image plane orientation data including orientations of standard view planes derived from the anatomical model in response to registration of the ultrasound image, and provide the image plane orientation data in a gating signal to the beamform controller;
wherein the beamform controller is configured to cause the matrix array probe to scan in real-time, the plurality of image planes using the image plane orientation data.

2. The diagnostic ultrasound system of claim 1, wherein the target anatomy further comprises a fetal heart; wherein the anatomical model further comprises a heart model; wherein the image registration processor registers a reference 2D fetal heart image to a plane of the anatomical model; and wherein the image plane orientation data identifies at least one standard view image plane.

3. The diagnostic ultrasound system of claim 2, further comprising a user control by which a user selects a plurality of standard views.

4. The diagnostic ultrasound system of claim 3, wherein the reference 2D fetal heart image further comprises a 4-chamber view.

5. The diagnostic ultrasound system of claim 4, wherein the at least one standard view image plane is that of an LV outflow tract, RV outflow tract, 5-chamber view, 3-vessel view, or a tracheal view.

6. The diagnostic ultrasound system of claim 5, wherein the display simultaneously displays real-time ultrasound images of a plurality of standard views, and wherein the display further display an icon graphic of a heart indicating the relative orientation of the plane of at least one real-time ultrasound image of the fetal heart.

7. A method for ultrasonically imaging a plurality of different selected image planes of a target anatomy in real-time comprising:

selecting a plurality of mutually different image planes of a target anatomy, a first image plane being one of the selected image planes;

positioning a matrix array probe at an acoustic window to the target anatomy;

acquiring a 2D image of the first image plane of the target anatomy;

registering the 2D image to data of an anatomical model of the target anatomy;

identifying orientation data of a second image plane of the target anatomy in response to registering the 2D image of the first image plane, the second image plane being another one of the selected image planes, wherein the orientation data include plane coordinates of the second image plane identified in the anatomical model data;

controlling, with a beamform controller, the matrix array probe to scan the first image plane and the second image plane in real-time using the orientation data, the orientation data being coupled in a gating signal to the beamform controller; and simultaneously displaying ultrasound images of the first image plane and the second image plane in real-time.

8. The method of claim 7, wherein the target anatomy further comprises a fetal heart, wherein the anatomical model further comprises a heart model, and wherein the first image plane and the second image plane further comprise image planes of standard views of a fetal heart.

9. The method of claim 7, further comprising displaying an icon graphic which identifies the relative orientations of one of the planes and the target anatomy.

10. The method of claim 7, further comprising: adapting the anatomical model to patient characteristics.

11. The method of claim 10, further comprising: entering patient characteristic data into an ultrasound system, and adapting the anatomical model to the entered patient characteristic data.

12. The method of claim 11, wherein adapting the anatomical model to the entered patient characteristic data further comprises selecting the data of the anatomical model in response to the entered patient characteristic data.

13. The method of claim 10, wherein adapting the anatomical model further comprises warping or morphing the data of the anatomical model to the 2D image.

14. A method for ultrasonically imaging a plurality of different selected image planes of a target anatomy in real-time comprising:

selecting a plurality of mutually different image planes of a target anatomy;

positioning a matrix array probe at an acoustic window to the target anatomy;

acquiring a volume image dataset of the target anatomy;

registering at least one plane of the volume image dataset to data of an anatomical model of the target anatomy;

identifying orientation data of the plurality of selected image planes of the target anatomy in response to registering the at least one plane of the volume image dataset, wherein the orientation data include orientations of standard view planes identified in the anatomical model data;

controlling, with a beamform controller, the matrix array probe to scan the plurality of selected image planes in real-time using the orientation data, the orientation data being coupled in a gating signal to the beamform controller; and simultaneously displaying ultrasound images of the plurality of selected image planes in real-time.

15. The method of claim 14, further comprising:

periodically acquiring another volume image dataset of the target anatomy; and updating the orientation data in response to the another volume image dataset.

* * * * *